United States Patent [19]

Christner et al.

[11] Patent Number: 5,169,771

[45] Date of Patent: Dec. 8, 1992

[54] METHOD FOR MAKING A SEDIMENTATION-RESISTANT STABLE ENZYME DISPERSION

[75] Inventors: Juergen Christner, Seeheim-Jugenheim; Hermann Plainer, Reinheim; Roland Reiner, Darmstadt, all of Fed. Rep. of Germany

[73] Assignee: Röhm Gmbh, Darmstadt, Fed. Rep. of Germany

[21] Appl. No.: 568,468

[22] Filed: Aug. 15, 1990

[30] Foreign Application Priority Data

Aug. 18, 1989 [DE] Fed. Rep. of Germany ....... 3927286

[51] Int. Cl.⁵ .......................... C12N 9/96; C12N 9/50
[52] U.S. Cl. ..................................... 435/188; 435/219
[58] Field of Search .......................... 435/188, 11, 219

[56] References Cited

U.S. PATENT DOCUMENTS

| | | | |
|---|---|---|---|
| 3,741,902 | 6/1973 | Barrett | 435/263 |
| 4,517,101 | 5/1985 | Williams et al. | 435/104 |
| 4,540,506 | 9/1985 | Jacobson et al. | 424/72 |
| 4,806,479 | 2/1989 | Kegel et al. | 435/244 |
| 4,923,981 | 5/1990 | Weibel et al. | 424/439 |
| 4,943,530 | 7/1990 | Christner et al. | 435/188 |

FOREIGN PATENT DOCUMENTS

| | | | |
|---|---|---|---|
| 1808834 | 7/1969 | Fed. Rep. of Germany . | |
| 1-104170 | 4/1989 | Japan | 435/188 |
| 1-104171 | 4/1989 | Japan | 435/188 |
| 1-104173 | 4/1989 | Japan | 435/188 |
| 659613 | of 1979 | U.S.S.R. | 435/188 |
| 2201960 | 9/1988 | United Kingdom . | |

OTHER PUBLICATIONS

Martinek, et al., *The Stabilization of Enzymes*, Russian Chemical Review, 1980, pp. 385-404.
Enzyme Microb. Technol., vol. 1, Apr. 1979, pp. 74-82; Torchilin et al.
"Fatty Acid Synthetase from Pig Liver", Dutler et al., Eur. J. Biochem. 22 (1971) 203-212.
"Neutral Salts: The Generalty of Their Effects on the Stability of Macromolecular Configurations", Science 145, Aug. 7, 1964.
"The Chemistry of Protein Denaturation", Chem. Rev. 34 (1944) 157-265.
American Heritage Dictionary of the English Language, Amer. Heritage Publishing Co., Inc. New York, 1975 p. 8.
The Random House Dictionary of the English Language, Unabridged, Random House, New York 1967, p. 9.

*Primary Examiner*—David M. Naff
*Assistant Examiner*—Mike Meller

[57] ABSTRACT

A method for making a stable aqueous liquid formulation containing at least one enzyme having proteolytic activity is disclosed. The method involves precipitating the enzyme from an aqueous medium with a salt to form a dispersion of the enzyme. The dispersion has a density of 1.22 g/cm³ to 1.23 g/cm³ due to the use of the salt. This process yields a sedimentation-resistant stable enzyme dispersion.

15 Claims, No Drawings

METHOD FOR MAKING A SEDIMENTATION-RESISTANT STABLE ENZYME DISPERSION

The present invention relates to methods for making aqueous liquid enzyme formulations in the form of directly usable preparations and to such formulations, and particularly to formulations of enzymes having proteolytic activity, such as the pancreatic complex, and methods for making the same.

Liquid enzyme preparations have achieved a certain preferential position in the utilization of enzymes. This is attributable in part to their safety. (See H. J. Rehm & G. Reed, ed., *Biotechnology*, vol. 7a, "Enzyme Technology", pp. 722 and 731, Verlag Chemie, Weinheim, New York 1987.)

Liquid enzyme preparations have the undeniable advantage of being dust free, which reduces the danger of allergic reactions. On the other hand, the risk of microbial contamination is increased, and aqueous liquid enzyme formulations therefore generally contain a preservative or a support that lowers the "water activity" for microbiological growth.

A further practical advantage of liquid preparations is that they are easier to dose than are the solid preparations of the prior art.

However, microbial contamination is not the only cause of the deterioration of enzymes in liquid formulations over a period of time. Whenever proteolytic enzymes are involved, either as main enzyme or as an impurity, self-digestion of the enzymes is likely to occur. The attendant loss of activity, usually rapid, is very high in the presence of pancreatic proteases and is difficult to avoid even with very low water activity. One alternative is the covalent bonding of proteases to support materials. Apart from the high cost of enzymes bonded to a support, however, purposeful utilization of immobilized enzymes is predicated on relative mobility of the substrates to be degraded, a condition which in the leather industry, for example, is not fully satisfied. On the other hand, enzyme mixtures which are not covalently bonded but are incorporated in microcapsules, filaments, or crosslinked polymer gels, for example, are autolytically broken down or cleaved by proteases, respectively, much like soluble enzymes. (See *Ullmanns Enzyklopadie der technischen Chemie*, 4th ed., vol. 10, p. 544, Verlag Chemie, 1975.

The problems attending the processing of pancreas are aggravated by the fact that, because of their zoogenetic origin, pancreatic juices in particular have a high germ loading to begin with.

As is known, enzymes having different functions coact in the digestive system. The pancreatic protease preparations commonly used industrially therefore are mixtures of trypsin (EC 3.4.21.4), chymotrypsin (EC 3.4.4.5), and various peptidases (e.g. EC 3.4.4.7) in solid form which may contain amylase (EC 3.2.1) and lipase (EC 3.1.1.3) as accompanying enzymes. Such preparations are generally manufactured by precipitation of freshly expressed pancreatic juice with salt, or from residues of insulin production. Through extremely gentle dehydration of the whole glands, the so called pancreatin is obtained in which the proteases are predominantly present in the form of inactive precursors and which has a very high lipase content. Before they can be used, such preparations have to be activated, for example through autolysis or by the addition of enterokinases or acidic fungal proteases or the like. (See *Ullmanns Enzyklopadie der technischen Chemie*, 4th ed., vol. 10, pp. 515–537, Verlag Chemie, 1975; Kirk-Othmer, *Encyclopedia of Chemical Technology*, 3rd ed., vol. 9, pp. 173–224, Wiley-Interscience, 1980.)

The desire to have aqueous liquid enzyme formulations available with their substantial advantages and no such disadvantages as loss of activity and contamination has given rise to various attempts involving solutions, such as blending with organic solvents (German patent 18 08 834, Hungarian patent 2,642, GDR patent 10,058), or nonaqueous liquid formulations. Up to now, however, these attempts have not been successful in every respect, particularly so far as enzymes with proteolytic activity, and especially pancreatic enzymes, are concerned. (See German patent 37 04 465 and U.S. Pat. No. 3,741,902, for example.) Liquid formulations in organic media have the disadvantage that preparation of the enzymes in dry form can hardly be circumvented and that the organic media best suited, for example, propylene carbonate, are too expensive.

Thus, there has still been a need to provide sufficiently stable aqueous liquid formulations of proteolytically active enzymes, and especially of the pancreatic complex, that are environmentally safe, yet not too expensive for industrial use, and particularly for use in the leather industry.

It has now been found that this object can be accomplished advantageously by the methods of the present invention.

The method of the invention for the manufacture of aqueous liquid enzyme formulations consists in precipitating the enzymes, present in an aqueous medium, in finely divided form in a manner known per se, and bringing about a sedimentation resistant, finely dispersed state of the enzymes through adjusting density in an aqueous medium.

As pointed out, the method lends itself to use with aqueous enzyme preparations of proteases, enzyme complexes with proteolytic activity, enzymes such as amylases, lipases, etc., having accessory proteolytic activity, and especially the pancreatic complex (pancreatin).

By enzymes having proteolytic activity are meant, in the first place, the endopeptidases ("proteases", EC 3.4), the industrially used enzymes being of primary interest for the purposes of the present invention. (Kirk-Othmer, loc.cit., vol. 9; K. Aunstrup, in *Industrial Aspects of Biochemistry*, B. Spencer, ed., vol. 30 (I), pp. 23–46, North Holland, 1974.)

Proteases are classified into the following groups:
(a) Animal-derived proteases, for example,
  (1) rennin (EC 3.4.23.4) and
  (2) pancreatic proteases, such as
    pancreatin, and particularly trypsin and chymotrypsin (optimal pH range, about 7 to 10),
    pepsin (EC 3.4.23.1) (optimal pH, about 1.5 to 4.0),
    cathepsin (EC 3.4.23.5) (optimal pH, about 4.0 to 5.0);
(b) plant-derived proteases, for example,
  (1) papain (EC 3.4.22.1) (optimal pH, about 5.0 to 8.0),
  (2) ficin (EC 3.4.22.3) (optimum pH, about 4.0 to 9.0),
  (3) bromelain (EC 3.4.22.4 and 3.4.22.5) (optimal pH, about 5.0 to 7.0);

(c) microbially derived proteases (see L. Keay in "Process Biochemistry", 1971, 17-21), for example,
  (1) proteases from such Bacillus species as *B. subtilis, B. licheniformis, B. alkalophilus, B. cereus, B. natto, B. vulgatus,* and *B. mycoides,*
  (2) from Streptococcus species,
  (3) from Streptomyces species such as *S. fradiae, S. griseus,* and *S. rectus,*
  (4) from Aspergillus species such as *A. flavus-oryzae, A. niger, A. saitori,* and *A. usamii,*
  (5) from Mucor and Rhizopus species such as *M. pusillus* and *M. mietrei,*
  (6) from Endothia species such as *E. parasitica,*
  (7) from Trametes species such as *T. sanguinea.*

In addition to being classified by source, proteases are classified on the basis of the point of attack (exo- vs. endoenzymes) and of the active site (serine proteases, inhibited by DFP; sulfhydryl enzymes).

Of great practical importance is also the pH dependence of enzyme activity.

From a practical point of view, proteases are therefore classified as follows:

(i) Alkaline proteases (optimal pH ranging from about pH 7.5 to 13), particularly alkaline bacterial proteases (EC 3.4.21), most of which are of the serine type, and alkaline fungal proteases.

(ii) Neutral proteases (optimal pH ranging from pH 6.0 to 9.0), particularly neutral bacterial proteases (EC 3.4.24), which belong to the metalloenzymes, and fungal proteases, for example, Bacillus proteases, Pseudomonas proteases, Streptomyces proteases, and Aspergillus proteases.

(iii) Acid proteases (optimal pH ranging from pH 2.0 to 5.0) (EC 3.4.23), particularly acid fungal proteases, for example, from Rhizopus species, Aspergillus species, Penicillium species, Mucor species, *Impex lacteus,* and *Endothia parasitica.*

Casein (Löhlein-Volhard, Kunitz and Laskowski method, see below), hemoglobin (Anson method, see below), or gelatins (viscosimetric method) are suitable for use as substrates in the analysis of commercial products. The proteolytic activity is usually determined by the Löhlein-Volhard method, as modified by the TEGEWA in "Leder", 22, 121-126, (1971). One Löhlein-Volhard unit (LVU) is equal to the amount of enzyme which under the test conditions (1 hour, 37° C.) produces in 20 ml of casein filtrate an increase in hydrolysis product corresponding to an equivalent of $5.75 \times 10^{-3}$ ml of 0.1N NaOH. The proteolytic activity of enzymes is frequently also determined by the Anson hemoglobin method. (M. L. Anson, J. Gen. Physiol., 22, 79 [1939].)

Proteases are industrially used in the manufacture of leather, in detergents and in dry cleaning, in desizing, in cheese making, in meat tenderizing, in the stabilization of beer, etc.

As mentioned earlier, also of interest are enzyme complexes having proteolytic activity and enzymes with accessory proteolytic activity. These include amylases, and particularly alpha-amylases (see Fischer and Stein, in *The Enzymes,* 2nd ed., P. D. Boyer et al., vol. IV, pp. 313-334, Academic Press), which as commercial preparations usually contain proteases as accompanying enzymes. These alpha-amylases are of animal, plant, or microbial origin. Pancreatic amylases, bacterial amylases, and fungal amylases, for example, are preferred.

The range of activity of alpha-amylases (that is, amylases which cleave the alpha-1,4-glucosidic bond within amylose or amylopectin) from various sources extends from pH 3.5 to pH 9.0. Alpha-amylase derived from pancreas is active over the pH range from 5.5 to 9.0, the pH optimum being about 7.2 Alpha-amylase derived from bacteria has a range of activity extending from pH 4.5 to pH 8.5, the pH optimum for liquefying alpha-amylase rangeing from 6.5 to 7.0, and that for saccharifying alpha-amylase ranging from 4.8 to 5.2. The range of activity of fungal alpha-amylase is 3.5 to 7.0 (pH optimum 5.0) and that of alpha-amylase from malt, 4.5 to 7.0 (pH optimum 4.7). (see Ulmanns, loc. cit., vol. 10, p. 507)

The production of amylases from Bacillus species, such as *B. subtilis, B. mesentericus, B. polymixa, B. amyloliquefaciens,* and *B. licheniformis;* from fungi, and particularly from Aspergillus species such as *A. niger, A. phoenicis, A. oryzae,* and *A. awamori;* from Mucor species such as *M. rouxianus;* from Rhizopus species such as *R. delemar, R. oryzae,* and *R. japonicus;* and from Endomyces species such as *E. fibuliger* is of steadily increasing importance. Amylases are used in the food sector (see H.-J. Rehm & G. Reed, ed., *"Biotechnology",* vol. 5, Verlag Chemie, 1983; B. Spencer, ed., *"Industrial Aspects of Biochemistry",* vol. 30, part I, pp. 139-186, 213-260, Elseviers, 1973), in the liquefaction of starch, in the production of malt and of ethanol, in desizing, in the manufacture of leather, and so forth. The activity of alpha-amylases can be determined by the method of Sandstedt, Kneen & Blish (Cereal Chem. 16, 172 [1939] and Technical Bulletin No. 1024, U.S. Department of Agriculture) using starch as the substrate. One amylase unit (=one SKB unit) is the amount of enzyme which at 30° C. and under the other specified reaction conditions is capable of dextrinizing 1 g of soluble starch in 1 hour.

The method of Willstätter is also used to determine the activity of pancreatic amylase. (Hoppe-Seylers, Z. physiol. Chem. 126, 143 [1923].). One Willstätter amylase unit is defined as 100 times the amount of enzyme which under the specified test conditions cleaves starch at such a rate that the mononuclear reaction constant is equal to 0.01.

Also within the scope of the process of the invention is its application to lipases (EC 3.1.1.3) having accessory proteolytic activity. As is known, lipases are carboxyl esterases which split esters of glycerol in aqueous emulsion.

Lipases may be classified as follows:

Pancreatic lipases, which are contained in the pancreatic enzyme complex as industrially important accompanying enzymes in addition to esterases, proteases, and amylases. The pH optimum (against olive oil) ranges from 7 to 8.5; the range of activity extends from pH 6.5 to pH 9.5. Lipases are generally regarded as very unstable, particularly to proteolytic breakdown by accompanying proteases.

Microbial lipases, for example, from *Pseudomonas fragii,* Aspergillus species (e.g. *A. luchuensis*), *Candida cylindracea, Geotrichum candidum, Humicola languinosa, Mucor pusillus,* Penicillium species (e.g. *P. chrysogenum* and *P. oxalicum*), and Rhizopus species (*R. nigericans* and *R. oryzae*). These lipases generally have a pH optimum at a pH value above 7.0.

The activity of lipases is conventionally determined using olive oil as substrate, but also with triacetin and tributyrin. (See M. Sémériva et al., Biochemistry 10, 2143 [1971]; *Pharmaceutical Enzymes,* edited by R. Ruyssen and A. Lauwers, 1978 [FIP].)

If lipolytic activity is expressed in kilo lipase units (KLCA), tributyrin is used as substrate under standard conditions (40° C., pH 5.5). (See M. Sémériva, loc. cit.)

Lipases are used in waste disposal, in the leather industry and in the food sector, to the extent permitted by their instability.

A particularly preferred subject of the process of the invention is the pancreatic complex. In the pancreas, trypsinogen represents approximately 23 weight percent, and chymotrypsinogen approximately 10 to 14 weight percent, of the total protein content.

The enzymes of the pancreatic complex which here are of special interest have already been characterized above. The enzymes ribonuclease (EC 2.7.7.16), deoxyribonuclease (EC 3.1.4.5), chymotrypsinogen B, and chymotrypsinogen as well as trypsinogen can be isolated from bovine pancreas.

The isolation of enzymes from the pancreatic complex has been described in detail in the literature. (See, for example, Ullmanns, loc. cit., vol. 10, pp. 535–537.)

The method of the invention involves the following.

(A) Isolation from the Pancreatic Complex

The process of the invention follows to some extent the prior art isolation methods. (See Ullmanns, loc. cit., vol. 10, pp. 536–537.)

1. Extraction

Isolation advantageously starts at the pancreas, predominantly of hogs or cattle, immediately after slaughter. About 100 pancreas glands, for example, can be processed in one batch by removing as much fat and connective tissue as possible from the glands immediately after slaughter and then homogenizing the glandular tissue by means of a food mill, for example. This is followed immediately by extraction, advantageously with about double the volume (about 60 liters) of 0.25N sulfuric acid, at 5° C. for 18-24 hours. After adding filter flakes, the extract is put through a filter press, advantageously a plate and frame press. The filter plates can be discarded.

2. Processing

Substantially fat free filtered pancreas extract is precipitated with a large amount of sodium sulfate or ammonium sulfate ("A salt"), preferably added quickly, at room temperature. The amount of solid anhydrous A salt added is advantageously about 50±2 percent by weight of the liquid extract.

It may be advantageous to crush the precipitate to a finer degree of subdivision by vigorous stirring, for example by means of a toothed-disk agitator. However, in many cases this may be dispensed with since adding the A salt quickly will cause the pancreatic enzymes to be precipitated in finely divided form.

To formulate and standardize the product to a specific desired activity, it is diluted, if necessary, with isotonic A-salt solution using, for example, 38.3 kg of A salt per 61.7 kg of water. The density of the aqueous enzyme preparation should be set to 1.22 to 1.23 gm/cm$^3$ by adding solid A salt or water. Experience with the pancreatic complex has shown that the enzyme suspension will remain substantially resistant to sedimentation only over a narrow density range, which on the basis of the results obtained so far is 1.22 to 1.23. For the purposes of the invention, it is therefore mandatory that the requisite narrow density range be adhered to. This rule holds also for crude extracts of enzymes from other sources, as described above.

3. Further Formulation

The isotonic standardization of the culture filtrates according to the invention, especially those of pancreatic origin, makes it possible to provide sedimentation-resistant formulations which can be relied on to meet requirements for a period ranging from days to weeks, thus satisfying in many cases the conditions for commercial utilization. However, the resistance to sedimentation may be reduced by evaporation of the carrier liquid (water) or by sharp temperature changes, through the attendant density variations or fluctuations. The enzyme suspension may then break (cream or settle). However, stringent practical requirements call for fully sedimentation-resistant and homogeneous enzyme preparations.

Surprisingly, adequate thickening of the strongly electrolytic enzyme suspension (containing, for example, 38.3 weight percent of A salt) can be brought about only by the use of at least one xanthan-based thickening agent.

Suitable for use are, in particular, xanthan (polysaccharide B-1459, Keltrol F. Kelzan; see Kirk-Othmer, *Encyclopedia of Chemical Technology,* 3rd ed., vol. 12, pp. 62–66, J. Wiley & Sons, 1980; Rees & Welch, Angew. Chemie 89, 228–239 [1977]), or other xanthan-based thickeners. For example, thickening with a specially modified xanthan derivative (e.g., K1A96, an anionic heteropolysaccharide manufactured by Kelco, San Diego, Calif.) in a concentration from 0.1 to 5 percent, and preferably from 0.1 to 1 percent, results in viscosities ranging from 200 to 1000 mPa s with a 38.3 weight percent A-salt solution.

As a rule, thickening with a 0.1 to 5 weight percent solution of xanthan or its derivatives in a solution of 38.3 weight percent of solid A salt will give very good results, especially when the xanthan is worked in very rapidly, for example, at peripheral speeds ranging from 1 to 5 meters/second, with shearing action. This xanthan solution should be isotonic with the A-salt solution used for precipitation. It may be added directly to the filtered pancreas extract precipitated with A salt to obtain the desired final activity of the enzyme. However, it has been found that even with non-isotonic conditions, for example in the wider density range of 1 to 1.5 gm/cm$^3$, a degree of thickening is obtained that is sufficient to give sedimentation resistant enzyme formulations. It should be noted that when a pancreas suspension precipitated with A salt is diluted with the thickened isotonic A-salt solution, the viscosity is reduced by about 50 percent. But even with the remaining viscosity of from 100 to 500 mPa·s, fully sedimentation-resistant and activity-stabilized homogeneous enzyme preparations are obtained.

(B) Isolation from Other Proteinase-Containing Crude Extracts

Other proteinase containing liquid extracts from fungal or bacterial cultures, for example, may be used in place of the liquid extract of pancreas. (Refer to the above data on enzymes.)

Moreover, the process of the invention may be applied to combination fungal proteinase/pancreatic proteinase or bacterial proteinase/pancreatic proteinase. Two options are:

(a) The various liquid culture extracts are mixed at from 5° C. to 10° C. and precipitation is effected immediately with A salt. The desired final activity is then obtained through isotonic dilution, optionally with thickened A-salt solution.

(b) The bacterial or fungal proteinase preparation (A-salt precipitation) is produced like the pancreas suspension but separately. The bacterial or fungal proteinase preparation, isotonic with the pancreas preparation, is then added, isotonically diluted for standardization if necessary, and stabilized with thickened isotonic A-salt solution if indicated.

In either case, a formulation that has both resistance to sedimentation and stable activity is obtained.

Because of their high electrolyte content, these enzyme suspensions do not usually have to be made stable to microbial degradation. On the other hand, there are no technical considerations that would militate against the addition of conventional preservatives.

In the light of past experience, the liquid medium r should have a density range of from 1.22 to 1.23 gm/cm$^3$ in the case of all enzymes in order that sedimentation resistance may be achieved. This applies also to the final formulation with thickening agents.

A better understanding of the present invention and of its many advantages will be had by referring to the following specific examples, given by way of illustration.

Density is determined by accurately weighing a defined quantity by volume in a calibrated graduated cylinder at 20° C.

Viscosity is determined with the Brookfield viscometer, also at 20° C.

EXAMPLES

Example 1

Preparation of an Isotonic Solution with a Density of from 1.22 to 1.23 g/cm$^3$ at 20° C.

61.7 kg of tap water are introduced into a stirred tank and mixed with 38.3 kg of anhydrous ammonium sulfate. The batch is stirred until all of the salt has dissolved. If the density of 1.22 to 1.23 g/cm$^3$ is not obtained, it can be obtained by adding salt or water.

Example 2

Preparation of an Aqueous Liquid Enzyme Formulation Comprising Pancreatic Enzyme 100 kg of a liquid extract having an activity of 30,100 LVU, as obtained after grinding, activation and extraction of pancreas, are introduced into a stirred tank and mixed with 50 kg of ammonium sulfate. Then the pancreatic enzymes are precipitated. The pancreatic enzyme suspension (29,600 LVU) has an average activity from 28,000 to 32,000 LVU/g (density, 1.22 to 1.23 g/cm$^3$). Any desired LVU activity level can be obtained by adding the isotonic ammonium salt solution from Example 1. The more dilute the enzyme preparation, the faster the precipitated enzyme will sediment.

1000 to 3000 LVU: Sedimentation after a few hours or days.

3000 to 9000 LVU: Sedimentation after one week or several weeks.

From ca. 16,000 LVU: Substantially resistant to sedimentation.

Loss of activity of a purely aqueous pancreatic enzyme solution after 6 weeks at 25° C.: 81%.

Loss of activity of precipitated enzyme suspension from pancreas after 6 weeks at 25° C.: 8.9%.

Example 3

100 kg of a clear aqueous solution of a fungal protease from *Aspergillus parasiticus* having an activity of 32,000 LVU are mixed at 16° C. with 50 kg of ammonium sulfate, the enzymes being thus precipitated. The enzyme suspension (31,400 LVU), having a density of from 1.22 to 1.23 g/cm$^3$, is diluted to the desired activity with the isotonic ammonium sulfate solution of Example 1. Enzyme preparations are so obtained which are resistant to sedimentation for several days.

Loss of activity of the enzyme suspension after standing for 6 weeks at 25° C.: 4.3%.

By comparison: Loss of activity of the purely aqueous fungal protease (without precipitation) after standing for 6 weeks at 25° C.: 62%.

Example 4

50 kg of liquid extract of pancreas (from Example 2) having an activity of 30,100 LVU and a temperature of 10° C. and 50 kg of liquid fungal protease extract (from Example 3) with an activity of 32,000 LVU and a temperature of 10° C. are mixed in a stirred tank. Immediately after mixing, 50 kg of ammonium sulfate are quickly added with stirring, the enzymes thus being precipitated. An enzyme suspension having an activity of 61,200 LVU is so obtained. The density ranges from 1.22 to 1.23 g/cm$^3$. The desired activity can be obtained by diluting with the isotonic ammonium sulfate solution from Example 1.

Loss of activity of the enzyme mixture (without precipitation) after 6 weeks at 25° C.: 74%.

Loss of activity of enzyme suspension (precipitated) after 6 weeks at 25° C.: 10.1%.

Example 5

50 kg of liquid aqueous bacterial protease (43,200 LVU, 10° C.) from *Bacillus licheniformis* and 50 kg of liquid extract of pancreas from Example 2 (31,100 LVU, 10° C.) are mixed in a stirred tank, then mixed with 50 kg of ammonium sulfate. The enzymes are thus precipitated. An enzyme suspension with an activity of 35,400 LVU is so obtained. It has a density from 1.22 to 1.23 g/cm$^3$ and can be brought to the desired activity by diluting with isotonic ammonium sulfate solution (Example 1). After standing for 6 weeks at 25° C., the activity has decreased by 12%. In contrast, the activity of an unprecipitated enzyme mixture has declined by 88% under the same conditions.

Example 6

(a) 3 kg of a pancreatic enzyme precipitate (the dispersion from Example 2 having an activity of 29,600 LVU) are mixed with 26.6 kg of an isotonic ammonium sulfate solution. An enzyme suspension having an activity of 3,000 LVU which is resistant to sedimentation for 3 days is obtained. After standing for 6 weeks at 25° C., its activity has decreased by 8.7%.

(b) 3 kg of a fungal protease precipitate (the dispersion from Example 3) are mixed with 28.4 kg of an isotonic ammonium sulfate solution. An enzyme suspension having an activity of 3000 LVU which is resistant to sedimentation for 4 days is obtained. After standing for 6 weeks, its activity has decreased by 5.5%

30 kg of pancreatic protease suspension from Example 6 (a) having an activity of 3000 LVU are mixed with 30 kg of fungal protease dispersion from Example 6 (b), also with an activity of 3000 LVU. The mixture has an activity of 3000 LVU and a density of 1.22 g/cm$^3$. After standing for 6 weeks at 25° C., the activity has decreased by 9.8%. In contrast thereto, the activity of an unprecipitated mixture of the same enzymes declines by 88% under the same conditions.

Example 7

Production of a Fully Sedimentation Resistant, Readily Usable, Free Flowing Aqueous Enzyme Preparation (a) 60.7 kg of water are introduced into a stirred tank, and 1 kg of a xanthan based thickening agent (e.g., K1A96, manufactured by Kelco) is worked into it with a toothed-disk agitator (peripheral speed, 2 to 3 meters/second). Once the viscosity of the solution has increased to above 1000 mPa s, 38.8 kg of ammonium sulfate are added. The solution is stirred until the ammonium sulfate has substantially dissolved, with the viscosity decreasing to 480 mPa s.

(b) 3 kg of the precipitated enzyme suspension from Example 4 (fungal enzyme, 62,200 LVU) are added to 58.2 kg of the thickened ammonium sulfate solution from Example 7 (a) and homogeneously mixed therewith by means of the toothed-disk agitator. A fully sedimentation resistant enzyme suspension with an activity of 3000 LVU and a viscosity of 270 mPa s is obtained. While an unprecipitated enzyme mixture will exhibit a 74 percent loss of activity after standing for 6 weeks at 25° C., the appropriately thickened enzyme suspension shows only a 9.2 per cent drop in activity.

What is claimed is:

1. A method for making a stable aqueous liquid formulation containing at least one enzyme having proteolytic activity, which method consisting essentially of precipitating the enzyme from an aqueous medium with a salt selected from the group consisting of ammonium sulfate and sodium sulfate to form a dispersion of said enzyme in finely divided form in said aqueous medium, said dispersion having a density of 1.22 g/cm$^3$ to 1.23 g/cm$^3$, whereby a sedimentation-resistant stable enzyme dispersion is obtained.

2. A method as in claim 1 wherein the aqueous medium from which said enzyme is precipitated is an enzyme extract.

3. A method as in claim 1 wherein, in a further step, a xanthan-based thickening agent is subsequently added to said sedimentation-resistant stable enzyme dispersion to enhance its resistance to sedimentation.

4. A method as in claim 1 wherein said aqueous medium contains a plurality of enzymes from different sources to obtain a sedimentation-resistant dispersion of said plurality of enzymes.

5. A method as in claim 1 wherein said proteolytic enzyme is a protease.

6. A method as in claim 5 wherein said enzyme is of microbial origin.

7. A method as in claim 1 wherein said enzyme is a selected from the group consisting of amylases and lipases having accessory protease activity.

8. A method as in claim 1 wherein said enzyme belongs to the pancreatic complex.

9. A method as in claim 3 wherein said xanthan-based thickening agent is added in the form of an aqueous, isotonic solution containing ammonium sulfate or sodium sulfate.

10. A method as in claim 9 wherein said solution of xanthan-based thickening agent is produced by agitation with shearing forces.

11. A method as in claim 10 wherein said xanthan-based thickening agent is from 0.1 to 1 weight percent of said solution.

12. The method of claim 1, wherein the sedimentation resistant stable enzyme dispersion is admixed with at least one other sedimentation resistant stable enzyme dispersion to form a dispersion containing a plurality of enzymes.

13. A stable aqueous liquid enzyme formulation made by the method of claim 1.

14. A stable aqueous liquid enzyme formulation made by the method of claim 4.

15. A stable aqueous liquid enzyme formulation made by the method of claim 12.

* * * * *